United States Patent [19]

Svinkin

[11] Patent Number: 5,610,336
[45] Date of Patent: Mar. 11, 1997

[54] METHOD FOR ESTIMATING FREQUENCIES OF MACHINE FOUNDATIONS

[76] Inventor: Mark R. Svinkin, 13821 Cedar Rd. #205, Cleveland, Ohio 44118-2376

[21] Appl. No.: 370,290

[22] Filed: Jan. 9, 1995

[51] Int. Cl.⁶ ..................................... G01N 3/30
[52] U.S. Cl. .............................................. 73/594
[58] Field of Search ............................. 73/594, 12, 13, 73/579, 784

[56] References Cited

U.S. PATENT DOCUMENTS

| | | | |
|---|---|---|---|
| 3,224,253 | 12/1965 | McKay | 73/594 |
| 3,391,571 | 7/1968 | Johanson | 73/594 |
| 3,946,598 | 3/1976 | Towne et al. | 73/594 |
| 4,128,011 | 12/1978 | Savage | 73/594 |
| 4,856,318 | 8/1989 | Hogan et al. | 73/12.13 |

*Primary Examiner*—John E. Chapman

[57] ABSTRACT

A new method for pre-construction determinations of the natural frequency of damped vibrations of foundations under machinery with known vertical impact loads which will be installed on a soil base, comprising steps for impacting the soil base with a weight to create natural vibrations of said soil base, measuring the vibration responses on soil base, recording the vibration responses, conducting spectrum analyses over the range of the soil base vibration records, and, determining the dominant natural frequency of said soil base from the preceding step, which frequency is an estimate of the natural frequency of vertical damped vibrations of the machine foundation.

3 Claims, 3 Drawing Sheets

METHOD FOR ESTIMATING FREQUENCIES OF MACHINE FOUNDATIONS

FIELD OF THE INVENTION

The subject invention discloses a method for obtaining pre-construction estimates of the natural frequencies of damped vibrations for foundations, which will be built at a specific site to bear machinery with dynamic loads. More particularly, the invention pertains to the relationship between such foundation frequencies and the natural frequencies of the soil base at a construction site.

BACKGROUND OF THE INVENTION

I have made an invention in the technical area of soil dynamics, which is a method for making pre-construction estimates of the frequencies of foundations under dynamic machinery and equipment. It is known that the natural frequencies of foundations are the dominant parameters in design and specification of foundations for machinery having dynamic loads. Knowledge of the exact values of these frequencies allows more accurate computation of vibration amplitudes and enables engineers to avoid the conditions of resonance of foundation vibrations.

The calculated natural frequency for foundations can be obtained on the basis of dynamic features of the foundation-soil system: mass, stiffness, and damping. There is no singular, generally accepted opinion on the nature of these features. However, there have been many theoretical and experimental approaches for determination of the characteristics of the foundation-soil system, but the results of application of the various methods frequently do not give coincident results. See, for example, Barkan, D. D. (1962), *Dynamics of Bases and Foundations*, McGraw-Hill Book Co., New York; Richart, F. E., Hall, J. R., and Woods R. D. (1970), *Vibrations of Soil and Foundations*, Prentice-Hall, Inc., Englewood Cliffs, N.J.

Furthermore, dynamic loads on a soil base effectively induce elastic waves in a soil base. Methods for in-situ surface measurements of steady-state and transient soil vibrations are used for examinations of elastic soil properties. The spectrums of soil vibrations excited by impacts show a few maximums with the dominant frequency of surface waves.

Frequencies of elastic waves are stable quantities which have been found to be characteristic for the site investigated. Actually, these frequencies are the natural frequencies of the soil bases and the values obtained do not practically depend on conditions at the contact area where impacts are made directly on the soil.

See, also, the following patents.

U.S. Pat. No. 3,224,253, to McKay, discloses an apparatus for conducting tests for analysis of existing structures in situ.

U.S. Pat. No. 3,391,571, to Johanson, is an apparatus and method for determining the effectiveness of vibratory devices.

U.S. Pat. No. 3,946,598, to Towne, et al., pertains to measuring the dynamic parameters of soil by driving piles into that soil.

U.S. Pat. No. 4,856,318, to Hogan, et al., reveals a method and apparatus for determining the suitability of playground equipment.

SU Patent 0822024 discloses an apparatus for driving steel casings into soil for dynamic sounding. The standard SPT Test measures the number of impacts and the depth to which the casing is driven downward by a series of impacts.

SU 1629403 applies to impacts on frozen ground, before and during the thawing process and further measurements upon complete thawing of the ground.

U.S. Pat. No. 4,128,011 to Savage, disclosed a method and apparatus for the investigation of the soundness of existing structures.

Accordingly, a need exists for a method to estimate, before construction, the natural frequency of damped vibrations of a designed foundation under operative machinery loads. And therefore, the primary objective of this invention is the disclosure and teaching of such a method.

The method disclosed herein is based on the relationship between the natural frequencies of vertical damped vibrations of rigid bodies on soil bases and the natural frequencies of the soil bases. Use of the method provides a means for predicting by essentially accurate estimates the natural frequencies for machine foundations prior to their erection at a specific site.

SUMMARY OF THE INVENTION

I have found that the natural frequency of vertical damped vibrations of a rigid body mounted on a soil base coincides with the dominant natural frequency of the soil base. This finding was made by making impacts of certain magnitude directly on the soil base at the sites for planned construction of foundations for operative machinery with known dynamic loads, and simultaneously, measuring the soil vibrations nearby the contact area but beyond the zone of plastic deformations of the soil caused by the controlled impacts.

Records are made during such measurements. Then the dominant frequency of the soil base is determined by spectrum analyses of the soil vibration records derived from the tests. Thus, my method is a means for obtaining advance estimates of the natural frequencies of vertical damped vibrations for machine foundations prior to construction thereof.

The invention is a new method for pre-construction determinations of the frequency of natural vibrations of foundations under machinery with vertical impact loads which will be installed on a soil base. Specifically, the method comprises the steps of a) impacting the soil base with a weight to excite natural vibrations of said soil base from a specific input location and thereby producing vibration responses at an output location on the soil base; b) measuring the vibration responses at output locations on said soil base; c) recording the vibration responses at the output locations; d) conducting spectrum analyses over the range of the soil base vibration records derived in the preceding step; and, e) determining the dominant frequency of said soil base from the preceding step, and using that frequency as an estimate of the frequency of vertical damped vibrations of the machine foundation.

As used herein, the term, "soil base" signifies the soil stratifications immediately below ground surface or existing excavation, wherein said vibration input and output locations are limited to the area for future machine foundation installation, while the output locations are beyond the zone of plastic deformations of the soil base caused by an impact. The impacts excite vibrations of the soil base and output locations provide vibrations responses of the soil base in the area for future installation of the machine foundation.

In a more specific application of the method for pre-construction determination of the natural frequency of damped vibrations of foundations which will bear machinery with vertical impact loads, a ratio of the impact on the soil base to the vertical impact from dynamic loads, on the machine foundation to be constructed, is preferably a one to one ratio. In the alternative and more preferably, the ratio is less than one.

Furthermore, if spectrum analyses of vibration responses at the output location results in several frequency maximums with equal ordinates, which is highly unlikely, then the lowest frequency should be used; meaning that said lowest frequency is an estimate of the natural frequency of vertical damped vibrations of the foundation.

DETAILED DESCRIPTION OF THE PREFERRED METHOD OF THE INVENTION

Disclosed herein is a method to estimate the natural frequency of vertical damped vibrations of a rigid body mounted on a soil base. Such frequency essentially coincides with the dominant natural frequency of the soil base. The method is primarily accomplished by the steps comprising: executing impacts with certain magnitude directly on the soil at a place of future installation of a machine foundation and, simultaneously measuring the soil vibrations nearby the contact area but beyond the zone of plastic deformations of the soil. The dominant frequency of the soil base is determined by spectrum analyses of derived soil vibration records.

The findings which I have made indicate that the natural frequency of vertical damped vibrations of a foundation or other rigid body mounted on a soil base coincides with the dominant natural frequency of the soil base. Hence, this disclosure is a method for estimating natural frequencies of vertical damped vibrations of machine foundations before construction thereof.

Figure 1:
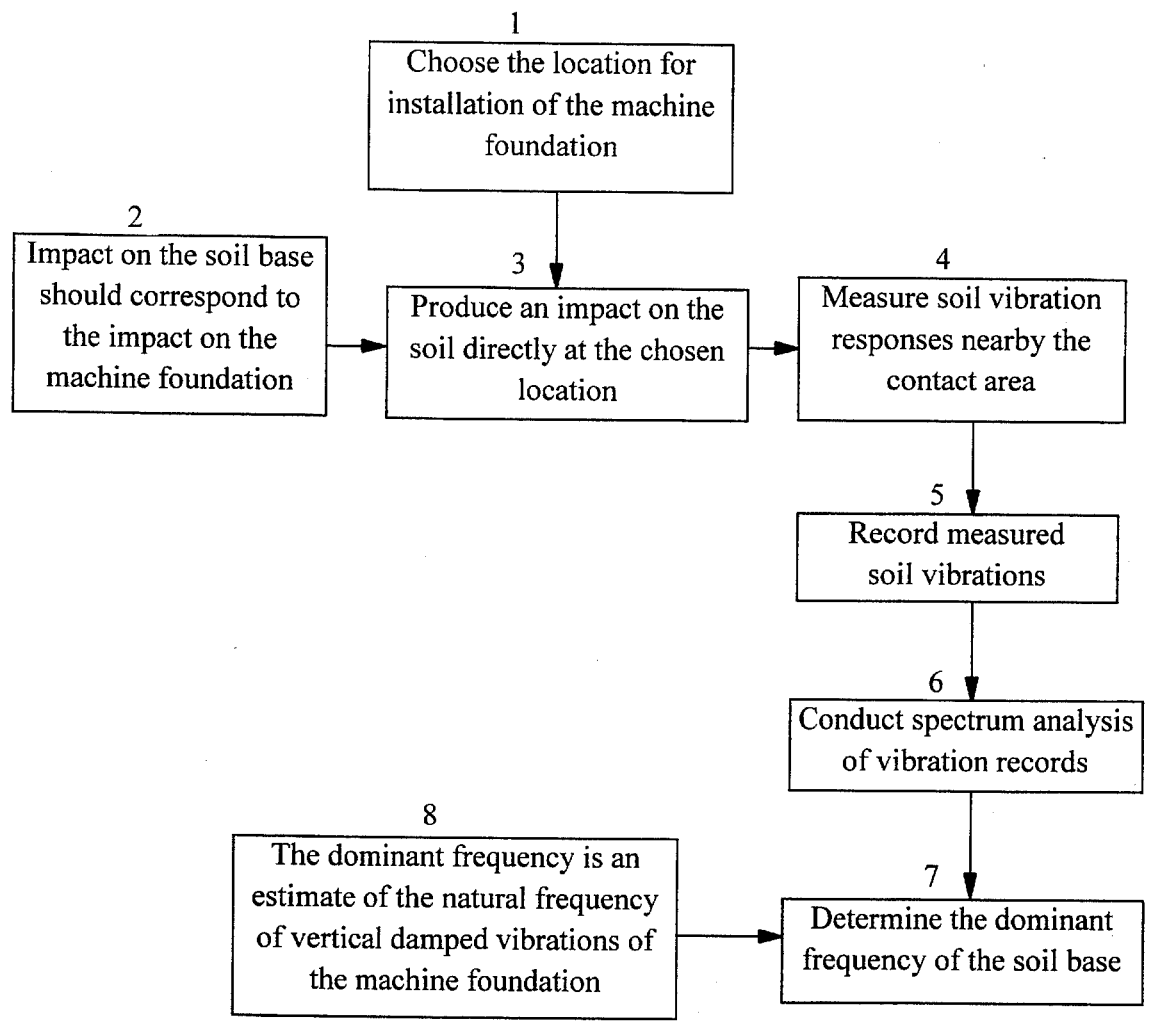
FIG. 1 shows flow diagram illustrating the test being performed.

FIG. 1 shows flow diagram illustrating the test being performed. Natural vibrations of a soil base are excited by impacts 3 directly on the soil base at the chosen location 1 for future installation of a machine foundation. For this purpose, the use of a steel weight and a bridge or mobile crane would be practical. Magnitudes of the impacts 2 should correspond to the values of known operative dynamic loads on the designated machine foundation. Impacts of a certain magnitude are made. While impacting the soil base, soil vibrations 4 are measured nearby the contact area, but beyond the zone of plastic soil deformations.

Records 5 are made during such measurements. Then spectrum analyses 6 are performed on the records of measured vibrations. The dominant frequency 7 of the soil base is calculated by the spectrum analyses of these soil vibration records. The dominant frequency of spectrums of soil vibrations is an estimate of the natural frequency 8 of vertical damped vibrations of the specified machine foundation.

The method disclosed herein comprises steps for a means to obtain advance estimates of the natural frequencies of vertical damped vibrations for machine foundations before construction of such foundations.

The invention teaches the sequence required for pre-construction determinations of the natural frequency of damped vibrations of foundations which will bear machinery having vertical impact loads, such foundations designed for installation on a soil base. Specifically, the method comprises the steps of a) impacting the soil base with a weight to excite natural vibrations of said soil base, the impacting conducted at a site for future construction of a foundation to support machinery with known dynamic impact loads and from a specific input location, thereby producing vibration responses at an output location on the soil base; b) measuring the soil vibration responses at output locations, which output location is near the impaction on said soil base but beyond the zone of plastic deformations of the soil base caused by the impacting step; c) recording the vibration responses at the output location; d) conducting spectrum analyses over the range of the soil base vibrations measured and recorded in records derived in the preceding step; and, e) determining the dominant frequency of the soil base from the preceding step, and using that frequency as an estimate of the natural frequency of vertical damped vibrations of the machine foundation.

It is preferable that the magnitude of the impaction essentially corresponds to a vertical impact of the dynamic loads to be borne by the designed machine foundation to be constructed at the site. More preferably, the magnitude of the impaction would be less than the vertical impact from dynamic loads on the machine foundation to be constructed at the site.

A more specific application of my method would include even greater control of magnitude of impaction, wherein a ratio of the impact on the soil base to the vertical impact from known dynamic loads on the machine foundation to be constructed, is preferably a one to one ratio. In the alternative and more preferably, the ratio is less than one.

If the spectrum analyses conducted over the range of vibration responses measured at the output location results in several frequency maximums with equal ordinates, which is highly unlikely, then the lowest frequency should be used; meaning that said lowest frequency equals the natural vertical vibration frequency of the foundation.

As used herein, "soil base" includes the soil stratifications immediately below ground surface or existing excavation. The vibration input and output locations are within the area designated for future machine foundation installation, while the output locations are beyond the zone of plastic deformations of the soil base caused by an impact. The impacts excite vibrations of the soil base and output locations provide vibrations responses of the soil base in the area for future installation of the machine foundation.

Figure 2:
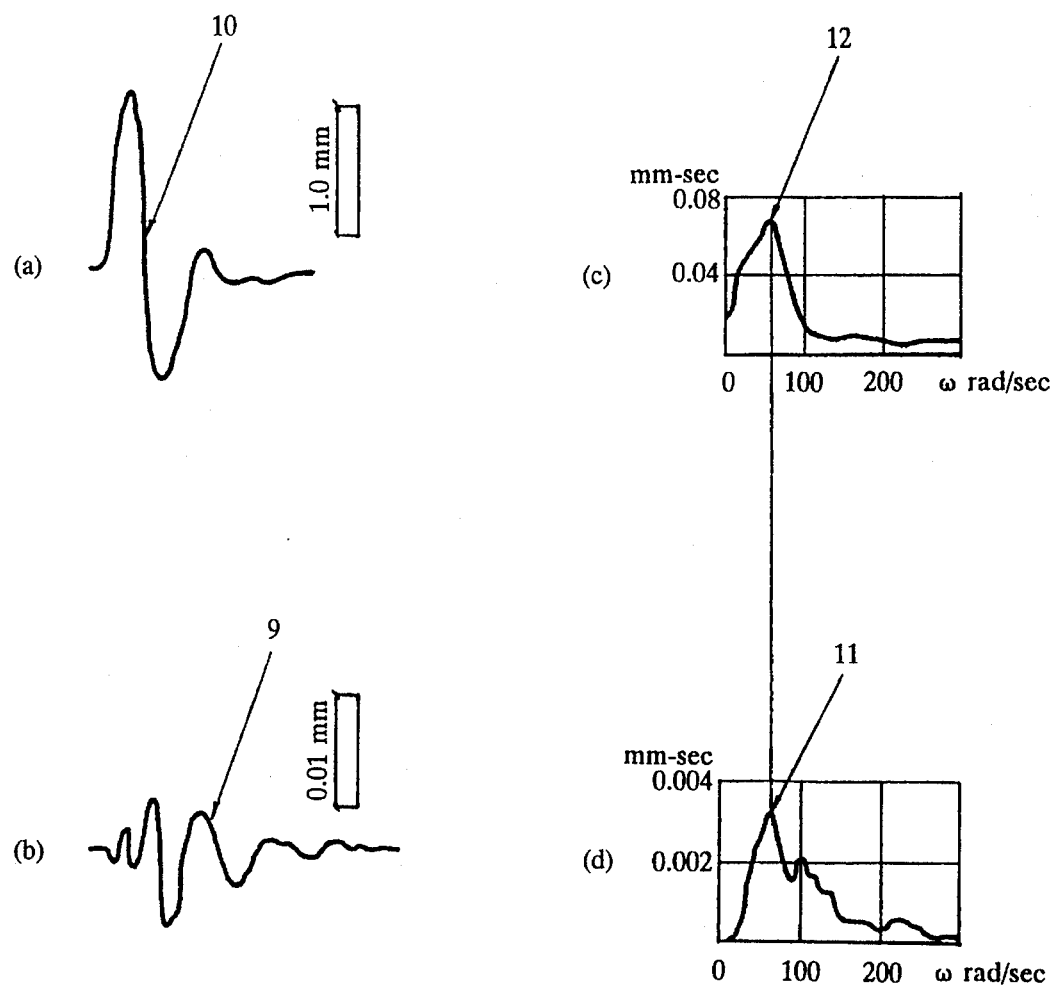
FIG. 2(A) shows foundation vibrations recorded from the impact described in the First Example.
FIG. 2(B) shows ground vibrations recorded by impacting the soil as described in the First Example.
FIG. 2(C) shows the frequency maximum determined by spectrum analyses of foundation vibrations in FIG. 2(A) according to the First Example, using the Fourier transform.
FIG. 2(D) shows the frequency maximum determined by spectrum analyses of ground vibrations in FIG. 2(B) according to the First Example, using the Fourier transform.
Figure 3:
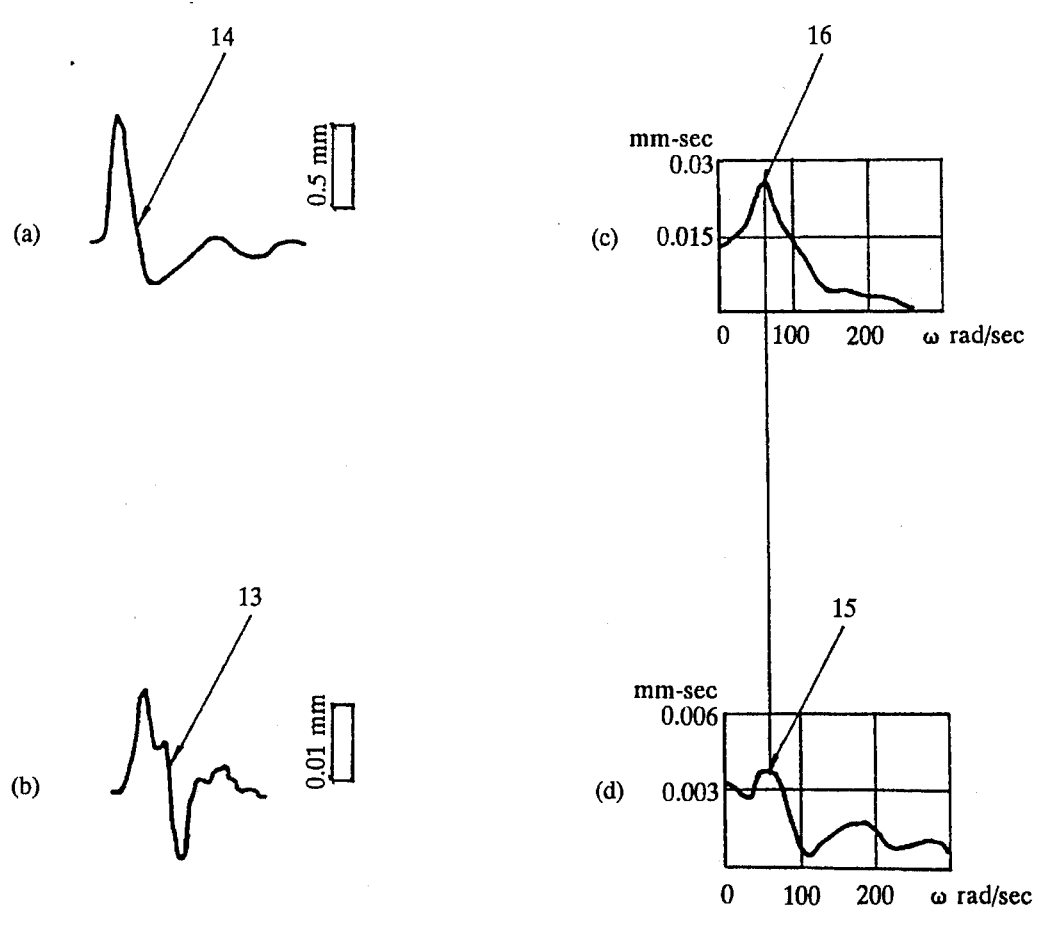
FIG. 3(A) shows foundation vibrations recorded from the impact described in the Second Example.
FIG. 3(B) shows ground vibrations recorded by impacting the soil as described in the Second Example.
FIG. 3(C) shows the frequency maximum determined by spectrum analyses of foundation vibrations in FIG. 3(A) according to the Second Example, using the Fourier transform.
FIG. 3(D) shows the frequency maximum determined by spectrum analyses of ground vibrations in FIG. 3(B) according to the Second Example, using the Fourier transform.

My invention is illustrated by two examples in FIG. 2 and FIG. 3.

EXAMPLE I

Reference is now made to the first example of FIG. 2. A foundation with foot area in square meters, of 12.3 m$^2$ under press-drop hammer with falling parts of 3.9 kN was placed on a site with the following soil conditions. Fill material with thickness of 1.5 m, brown-yellow, moist, middle density, fine sand was bedded to 8 m. The impulse of vertical force for impact on the soil was equal to 2.4 kN-sec and 34.7 kN-sec during machine operations. The ratio of these impulses was 14.5. Soil vibrations 9 and foundation vibrations 10 have spectrums 11 and 12 respectively with the same frequency maximum.

EXAMPLE II

Reference is now made to the second example of FIG. 3. A foundation with foot area in square meters, of 80.0 m$^2$ under forge hammer with falling parts of 7.1 kN was installed on a site with the following soil conditions. Fill material had a depth of 2 m. The soil was brown-yellow, loess loam with solid consistency and slump-prone properties bedded to between 5–6 m. Fine and powdered sand existed thereunder to 7–9 m. Another layer of yellow-brown, solid consistency loam was under the sand. There was no ground water to a depth of 10 m. The impulse of force for the impact on the soil was equal to 1.9 kN-sec and 78.5 kN-sec during machine operation. The ratio of impulse values was 41.3. Soil vibrations 13 and foundation vibrations 14 have spectrums 15 and 16 respectively with the same frequency maximum.

In general, soil bases are nonlinear systems. Over a certain range, however, the system behavior may be linear and if the system is restricted to this range it is possible to safely use the linear approach. This is the reason why the magnitude of impact on soil can be on order less than the value of operating machine impulse for the permissible vibration level. Still, this ratio might be more than ten for some soil conditions as it was shown in the above presented examples where it could be seen the good coincidence of natural frequency of vertical damped foundation vibrations with the corresponding natural frequency of the soil base.

On the first review, the invention may seem contrary to known concepts of soil dynamics. These concepts affirm that natural frequencies of foundation vibrations depend not only on soil properties but on foundation dimensions, masses, end embedment as well. However, there are no contradictions. Heterogeneous soil bases with various stratifications can have unequal dominant frequencies of natural vibrations for different locations of an industrial site. Machine foundations with different parameters, mounted on like soil bases, will have unequal natural frequencies of their vertical damped vibrations. In the case when the soil base of a site is a homogeneous medium with one dominant frequency of natural vibrations, all foundations with different parameters, installed on this site, will have the same natural frequency of their vertical damped vibrations. Similar case histories are observed in practice.

Hence, it is clear that there is no discrepancy between known concepts and my invention, but my invention explains the nature of the natural frequencies of vertical damped vibrations for machine foundations.

My invention opens a new viewpoint for familiar concepts on soil dynamics, and in particular, it gives the new method and greater precision of predictions for natural frequencies of vertical damped vibrations of foundations.

The foregoing description relates to a particularly useful method for estimating natural frequencies of machine foundations. While there have been illustrated and described what are at present considered to be steps for the preferred process of the present invention, it will be understood by those skilled in the art that various changes and modifications may be made, and equivalents steps may be substituted without departing from the true scope of the present invention. In addition, many modifications may be made to adapt a particular sequence of steps or substitute step to the teaching of the present invention without departing from the central scope thereof. Therefore, it is intended that the present invention not be limited to the particulars disclosed as the best mode contemplated for carrying out the present invention, but that the present invention include all methods and processes falling within the scope of the appended claims.

I claim:

1. A method for obtaining pre-construction estimates of the natural frequency of damped vibrations for a foundation which will carry machinery with known vertical impact loads, comprising the steps of:

impacting a soil base with a weight, said impacting being conducted at a site for future construction of a foundation to support machinery with known vertical impact loads;

measuring soil vibrations caused by the impacting of the soil base, said measuring conducted near the impaction, but beyond a zone of plastic deformations of the soil base caused by the impacting step;

recording the vibration responses;

conducting spectrum analyses over the range of vibrations measured and, recorded; and, determining from the spectrum analyses a dominant natural frequency of the soil base and using the dominant natural frequency as an estimate of the natural frequency of vertical damped vibrations of the foundation.

2. The method for determining natural frequency of damped foundation vibrations described in claim 1, wherein said impaction essentially corresponds to the known vertical impact loads on the machine foundation to be constructed at the site.

3. The method for determining natural frequency of damped foundation vibrations described in claim 2, wherein the magnitude of said impaction is equal or less than the known vertical impact loads on the machine foundation to be constructed at the site.

* * * * *